United States Patent
Staunig et al.

(10) Patent No.: US 12,305,212 B2
(45) Date of Patent: *May 20, 2025

(54) METHOD FOR THE HYDROXYLATION OF STEROIDS

(71) Applicant: PHARMAZELL GMBH, Raubling (DE)

(72) Inventors: Nicole Staunig, Vasoldsberg (AT); Kai Oliver Donsbach, Traunstein (DE)

(73) Assignee: PHARMAZELL GMBH, Raubling (DE)

( * ) Notice: Subject to any disclaimer, the term of this patent is extended or adjusted under 35 U.S.C. 154(b) by 116 days.

This patent is subject to a terminal disclaimer.

(21) Appl. No.: 17/908,507

(22) PCT Filed: Mar. 5, 2021

(86) PCT No.: PCT/EP2021/055617
§ 371 (c)(1),
(2) Date: Aug. 31, 2022

(87) PCT Pub. No.: WO2021/176068
PCT Pub. Date: Sep. 10, 2021

(65) Prior Publication Data
US 2024/0240221 A1    Jul. 18, 2024

(30) Foreign Application Priority Data
Mar. 6, 2020    (EP) .................................... 20161536

(51) Int. Cl.
*C12P 33/06*    (2006.01)

(52) U.S. Cl.
CPC .................................. *C12P 33/06* (2013.01)

(58) Field of Classification Search
None
See application file for complete search history.

(56) References Cited

U.S. PATENT DOCUMENTS

2003/0180742 A1    9/2003    Weiner et al.

FOREIGN PATENT DOCUMENTS

WO    03/52050 A2    6/2003

OTHER PUBLICATIONS

Database Uniprot [Online] EBI; Mar. 28, 2018 (Mar. 28, 2018), Xu Y. et al: "Genome sequence, genome mining and natural product profiling of a biocontrol bacterium Streptomyces mala ysiensis F913.", XP055928020.
Deshcherevska Ya N O et al. "Search and discovery of actinobacteria capable of transforming deoxycholic and cholic acids" Journal of Molecular Catalysis B: Enzymatic, vol. 133, 2016, DOI: 10.1016/J.MOLCATB.2016.12.010 ISSN: 1381-1177, XP085265327.
Fabio Tonin et al: "Latest development in the synthesis of ursodeoxycholic acid (UDCA): a critical review", Beilstein Journal of Organic Chemistry, vol. 14, Feb. 5, 2018 (Feb. 5, 2018), pp. 470-483, XP055657131.
Kollerov V V et al: "Deoxycholic acid transformations catalyzed by selected filamentous fungi", Steroids, vol. 107, 2016, pp. 20-29, XP0294406 I 2.
Kollerov V V et al: "Hydroxylation of lithocholic acid by selected actinobacteria and filamentous fungi", Steroids, vol. 78, No. 3, Jan. 18, 2013 (Jan. 18, 2013), pp. 370-378, XP028981316.

*Primary Examiner* — Robert J Yamasaki
(74) *Attorney, Agent, or Firm* — Workman Nydegger

(57) ABSTRACT

The present invention relates to an enzyme and method for the hydroxylation of a 7-deoxysteroid having the general formula (I)

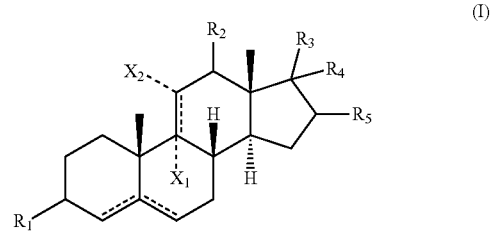

at position 7 to a steroid having the general formula (II)

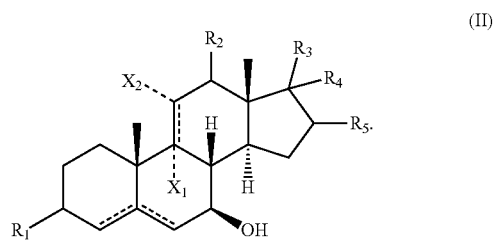

10 Claims, No Drawings
Specification includes a Sequence Listing.

METHOD FOR THE HYDROXYLATION OF STEROIDS

CROSS-REFERENCE TO RELATED APPLICATIONS

This Application is a 371 of International Patent Application No. PCT/EP2021/055617, filed Mar. 5, 2021, which claims the benefit of European Patent Application No. 20161536.6, filed Mar. 6, 2020, which are incorporated herein by reference in their entireties.

SEQUENCE LISTING

The instant application contains a Sequence Listing that has been submitted electronically in ASCII format and is hereby incorporated by reference in its entirety. Said ASCII copy, created on Jan. 27, 2023, is named "16785-324_2023-01-30_Sequence-Listing" and is 22.6 kb in size.

TECHNICAL FIELD

The present invention relates to means and methods for the hydroxylation of steroids.

BACKGROUND OF THE INVENTION 3,7,12-Trihydroxylated bile acids, such as, e.g., cholic acid (3α,7α,12α-trihydroxy-5β-cholanic acid) or ursocholic acid (3α,7β,12α-trihydroxy-5β-cholanic acid), are industrially important chemicals, among other things as starting materials for the manufacture of ursodeoxycholic acid (UDCA). Ursodeoxycholic acid is used, among other things, as a medicament for dissolving minor X-ray negative gallstones as well as for treating the liver diseases primary ciliary cirrhosis and primary sclerosing cholangitis.

The industrially most important source of 3,7,12-trihydroxylated bile acids is biliary fluid from gallbladders, which accumulate as slaughterhouse waste in meat production. Besides other animal species, the bile of cattle is often used. There is no industrially relevant total synthesis for 3,7,12-trihydroxylated bile acids. Since the production of bile acids is linked to another product (meat), the response to increased demands can only be very limited. For this reason, it is of great interest to use the raw material bile as efficiently as possible.

Since bile is an aqueous mixture of bile acids, lipids, cholesterol and other substances, the separation of the components during the extraction of bile acids is of particular importance. The bile acids, in turn, also constitute a mixture the components of which differ in the number and position of the hydroxyl groups. In addition to cholic acid, bovine bile also contains a significant proportion of deoxycholic acid, which differs from cholic acid in that the OH group is missing at position 7 (3α,12α-dihydroxy-5β-cholanic acid). Deoxycholic acid has a much lower commercial value than 3,7,12-trihydroxylated bile acids. Therefore, there is an industrial interest in converting deoxycholic acid into a 3,7,12-trihydroxylated bile acid by selectively introducing a hydroxyl group at position 7.

During hydroxylations, an oxygen atom is formally introduced into a (non-activated) C—H bond in an oxidation reaction. In organic chemistry, these are reactions that are very difficult to perform. OH groups are frequently introduced through detours, e.g., by adding water at a C=C double bond. The selective hydroxylation at a specific position of a complex molecule (such as, e.g., a bile acid) is problematic, since several chemically (almost) equivalent C—H bonds are present.

It is known that certain actinobacteria and filamentous fungi can catalyze the regio- and stereospecific hydroxylation of lithocholic acid ("LCA") at position 7β to ursodeoxycholic acid ("UDCA") (Kollerov et al., Steroids, 78 (3): 370-378 (2013); Tonin et al. (Beilstein Journal of Organic Chemistry, 14: 470-483 (2018)).

In addition, the hydroxylation of deoxycholic acid at position 7 by filamentous fungi (Kollerov et al., Steroids, 107: 20-29 (2016)) and actinobacteria (Deshcherevskaya et al., Journal of Molecular Catalysis B: Enzymatic, 133: p. 157-p. 165 (2016)) has been described.

It is an object of the present invention to provide means and methods of hydroxylating steroids, such as bile acids and derivatives thereof, which have a hydrogen and no hydroxyl group at position 7, specifically at this point.

SUMMARY OF THE INVENTION

The object according to the invention is achieved by using cytochrome P450 or a functional fragment thereof for the hydroxylation of a 7-deoxysteroid having the general formula (I)

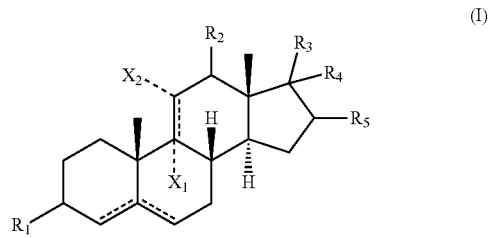

at position 7 to a steroid having the general formula (II)

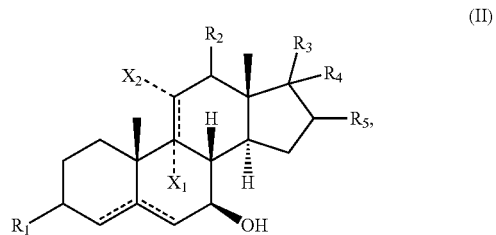

wherein
$X_1$ and $X_2$ are independently H, Cl, F, Br, I, $CF_3$, a $C_1$ to $C_6$ alkyl radical, OH, a $C_1$ to $C_6$ alkoxy radical, CN, $NO_2$, $N(R_6)_2$, an epoxy group, CHO or a $CO_2R_6$ radical, wherein
$R_6$ is —C(O)H, —C(O)$CH_3$, —C(O)$CH_2CH_3$, —C(O)($CH_2$)$_2CH_3$, —C(O)CH($CH_3$)$_2$, —C(O)($CH_2$)$_3CH_3$, —C(O)CH($CH_3$)$CH_2CH_3$, —C(O)$CH_2CH_2$($CH_3$)$_2$, —C(O)C($CH_3$)$_3$, —C(O)Ph, —C(O)$CH_2$Ph, $R_1$ and $R_2$ are independently H, OH, $OR_2$ or O, wherein
$R_7$ is —C(O)H, —C(O)$CH_3$, —C(O)$CH_2CH_3$, —C(O)($CH_2$)$_2CH_3$, —C(O)CH($CH_3$)$_2$, —C(O)($CH_2$)$_3CH_3$, —C(O)CH($CH_3$)$CH_2CH_3$, —C(O)$CH_3CH_2$($CH_3$)$_2$, —C(O)C($CH_3$)$_3$, —C(O)Ph, —C(O)$CH_2$Ph, $R_3$ is H, OH, $OR_8$, a $C_1$ to $C_{10}$ alkyl radical, a $C_1$ to $C_{10}$ alkenyl radical, —CHO, —C(O)(CH$_3$), —C(O)(CH$_2$OH), —CH(CH$_3$)C(O)CH$_3$, —CH(CH$_3$)((CH$_2$)$_2$CO$_2$R$_9$) or —CH(CH$_3$)((CH$_2$)$_2$CONHR$_9$), wherein $R_8$ is —C(O)H, —C(O)CH$_3$, —C(O)CH$_2$CH$_3$, —C(O)(CH$_2$)$_2$CH$_3$, —C(O)CH(CH$_3$)$_2$, —C(O)(CH$_2$)$_3$CH$_3$, —C(O)CH(CH$_3$)CH$_2$CH$_3$, —C(O)CH$_2$CH$_2$(CH$_3$)$_2$, —C(O)C(CH$_3$)$_3$, —C(O)Ph or —C(O)CH$_2$Ph, and $R_9$ is —CH$_3$, —CH$_2$COOH, —CH$_2$CH$_3$, —CH(CH$_3$)$_2$, —(CH$_2$)$_2$CH$_3$, —(CH$_2$)$_2$SO$_3$H, C(CH$_3$)$_3$, —(CH$_2$)$_3$CH$_3$, —CH(CH$_3$)CH$_2$CH$_3$, —CH$_2$CH$_2$(CH$_3$)$_2$, an aryl group or an alkylaryl group, $R_4$ is H, OH, or —$OR_{10}$, wherein $R_{10}$ is —C(O)H, —C(O)CH$_3$, —C(O)CH$_2$CH$_3$, —C(O)(CH$_2$)$_2$CH$_3$, —C(O)CH(CH$_3$)$_2$. —C(O)(CH$_2$)$_3$CH$_3$, —C(O)CH(CH$_3$)CH$_2$CH$_3$, —C(O)CH$_2$CH$_2$(CH$_3$)$_2$, —C(O)C(CH$_3$)$_3$, —C(O)Ph or —C(O)CH$_2$Ph, and $R_5$ is H, CF$_3$, a $C_1$ to $C_6$ alkyl radical, a $C_1$ to $C_6$ alkenyl radical, OH, O, or a $C_1$ to $C_6$ alkoxy radical, wherein the dashed line denotes an optional double bond, with the proviso that the B ring has no double bond if the A ring has a $C_4$-$C_5$ double bond, and the C ring has no double bond if $X_1$ and $X_2$ form an epoxy group, characterized in that the cytochrome P450 enzyme comprises an amino acid sequence which is at least 80%, preferably at least 90%, in particular 100%, identical to the amino acid sequence SEQ ID No. 1 or 2.

Surprisingly, it has been shown that cytochrome P450 and functional fragments thereof are capable of hydroxylating steroids such as cholic acid and, respectively, derivatives thereof having the formula (I) at position 7.

A further aspect of the present invention relates to a method of preparing a steroid, preferably a cholic acid, or a derivative thereof having the general formula (II) as defined above, comprising the step of converting a 7-deoxysteroid, preferably a 7-deoxycholic acid, or a derivative thereof having the general formula (I) with the cytochrome P450 according to the invention or a functional variant thereof.

DESCRIPTION OF THE EMBODIMENTS

Cytochrome P450 and functional variants thereof are surprisingly capable of selectively hydroxylating 7-deoxysteroids, such as, e.g., 7-deoxycholic acid, and derivatives thereof at position 7.

According to the present invention, the cytochrome P450 enzyme comprises an amino acid sequence which is at least 80%, preferably at least 90%, in particular 100%, identical to the amino acid sequence SEQ ID No. 1 or 2.

Cytochromes P450 catalyze monooxygenase reactions of a large number of endogenous as well as exogenous substrates. They are involved, among other things, in the metabolism of steroids, eicosanoids, fatty acids and bile acids as well as of exogenous substrates such as drugs, insecticides and chemical carcinogens.

Cytochromes P450 according to the present invention can be used, for example, from bacteria such as actinobacteria, in particular, for example, from the genus *Streptomyces*. In this case, the sequences can be isolated, for example, from genomic DNA or a cDNA library using known techniques.

The cytochromes P450 according to the present invention and, respectively, their functional variants can optionally be present in their original organism or can be isolated therefrom, or they are expressed recombinantly or produced synthetically. Recombinantly expressed polypeptides are preferably used according to the invention.

Various established microorganisms can be used for the recombinant expression of enzymes according to the present invention, such as, e.g., *Escherichia coli* (*E. coli*), *Bacillus subtilis*, *Saccharomyces cerevisiae* or *Pichia pastoris*. Appropriate protocols in this regard are described in detail in the relevant specialist literature or are known to a person skilled in the art.

According to the present invention, enzymes/polypeptides are preferably used as proteins recombinantly overexpressed in *E. coli*, with the corresponding cell lysates preferably being used either without further processing/purification or after relatively simple processing steps (e.g., centrifugation, precipitation, concentration or lyophilization). After the recombinant overexpression of the enzymes used, *E. coli* cells can alternatively also be used in the reaction directly without cell disintegration or, for example, after a freezing/thawing cycle. Suitable expression plasmids are known to a person skilled in the art and can often be purchased commercially.

"Functional variants" of cytochrome P450 can be fragments or mutational variants of cytochrome P450, wherein fragments of cytochrome P450 can also be referred to as "functional fragments". "Functional variants" of cytochrome P450 are capable of catalyzing the same reaction as the protein from which they have been derived. Whether a variant is functional, i.e., whether it catalyzes the same reaction as the protein from which it is derived, can be determined by establishing that the variant catalyzes the same reaction. For this purpose, there are established methods in the prior art or, respectively, those that are described herein. The conversion rates of substrates by the functional variants according to the invention can deviate from the conversion rates of the cytochrome P450 from which they have been derived.

"Derivatives of 7-deoxysteroids" comprise compounds derived from 7-deoxysteroids and having a wide variety of modifications, with one or several modifications at positions 3, 12 and 17 of the 7-deoxysteroid being particularly preferred. Such modifications preferably comprise substitutions as defined above.

According to a preferred embodiment of the present invention, $X_1$, $X_2$, $R_4$ and $R_5$ are H and $R_1$ und $R_2$ are independently H, OH, $OR_8$ or O, wherein
$R_8$ is —C(O)H, —C(O)CH$_3$, —C(O)CH$_2$CH$_3$, —C(O)(CH$_1$)$_1$CH$_3$, —C(O)CH(C$_1$—H$_3$)$_2$, —C(O)(CH$_2$)$_3$CH$_3$. —C(O)CH(CH$_3$)CH$_2$CH$_3$, —C(O)CH$_2$CH$_2$(CH$_3$)$_2$, —C(O)C(CH$_3$)$_3$, —C(O)Ph, —C(O)CH$_2$Ph, $R_3$ is a $C_1$ to $C_{10}$ alkyl radical, a $C_1$ to $C_{10}$ alkylen radical, —CH(CH$_3$)((CH$_2$)$_2$CO$_2$R$_9$) or —CH(CH$_3$)((CH$_2$)$_2$CONHR$_9$), wherein $R_9$ is —CH$_3$, —CH$_2$COOH, —CH$_2$CH$_3$, —CH(CH$_3$)$_2$, —(CH$_2$)$_2$CH$_3$, —(CH$_2$)$_2$SO$_3$H, C(CH$_3$)$_3$, —(CH$_2$)$_3$CH$_3$, —CH(CH$_3$)CH$_2$CH$_3$, —CH$_2$CH$_2$(CH$_3$)$_2$, an aryl group or an alkylaryl group.

According to a further preferred embodiment of the present invention, the aryl group is selected from the group consisting of a phenyl radical, a phenyl radical substituted with F, Cl, Br, NO$_2$ or CH$_3$ and a heteroaryl.

According to yet another preferred embodiment of the present invention, the alkylaryl group is selected from the group consisting of a benzyl group, a halogenated benzyl group, wherein the halogen is F, $C_1$ or Br, and a benzyl group substituted with NO$_2$.

According to a preferred embodiment of the present invention, $R_1$ is OH, $R_2$ is O or OH, $R_3$ is $CH(CH_3)((CH_2)_2CO_2R_5)$, $R_4$ is H, and $R_5$ is H.

According to another preferred embodiment of the present invention, the 7-deoxysteroid having the general formula (II) is selected from the group consisting of 3α,12α-dihydroxy-5β-cholane-24-acid, 3α,12β-dihydroxy-5β-cholane-24-acid, 3β,12α-dihydroxy-5β-cholane-24-acid, 3ß,12ß-dihydroxy-5ß-cholane-24-acid, 3ß-hydroxy-12-keto-5ß-cholane-24-acid, 3-keto,12ß-hydroxy-5ß-cholane-24-acid, 3-keto,12α-hydroxy-5β-cholane-24-acid, 3α-hydroxy-5β-cholane-24-acid, 3-keto-5β-cholane-24-acid, 30-hydroxy-5β-cholane-24-acid and esters of the respective acid.

The cytochrome P450 hydroxylase used, according to the invention, for the hydroxylation of 7-deoxysteroids and derivatives thereof having the general formula (I) to a steroid or a derivative thereof having the general formula (II) comprises an amino acid sequence which is at least 80%, preferably at least 85%, more preferably at least 90%, more preferably at least 95%, more preferably at least 96%, more preferably at least 97%, more preferably at least 98%, more preferably at least 99%, in particular 100%, identical to the amino acid sequence SEQ ID No. 1 or 2.

```
SEQ ID No. 1:
MLTTAETTSIAYPFNTAEGLALSERYEEARNRTGLLRVRMPYGEPAWLV

TRYADARLVLGDRRFSRAEALHHDEPRQSEGRPDSGILTMDPPDHTRLR

TLVAKAFTVHQVEKLRPWVRQLTHDLLDDLEAAGPPADLVDRYALPIPV

GVICAMLGVPQEDRPKFRVWSDAALSTSSLSAEQFARNTDELRAYMAGL

IEDHRRTPRDDIMTSLIEARDAGDRLSELELVDLCVGILVAGHETTATQ

IPNFVLTLLEHPDQLRRLREDPALIQGAVEELLRFVPLGVGAAQARYAT

EDIEVGGTLVRSGEPVLVAVGSANRDALRFDEPGVLNVARPTTQHLGFG

HGVHHCLGAPLARLELQEALGALITRFPGLRLAGDIEWKDRMLVRGPRV

MPIGW

SEQ ID No. 2:
MPYGEPAWLVTRYADARLVLGDRRFSRAEALHHDEPRQSEGRRDSGILT

MDPPDHTRLRTLVAKAFTVHQVEKLRPWVRQLTHDLLDDLEAAGPPADL

VDRYALPIPVGVICAMLGVPQEDRPKFRVWSDAALSTSSLSAEQFARNT

DELRAYMAGLIEDHRRTPRDDIMTSLIEARDAGDRLSELELVDLCVGIL

VAGHETTATQIPNFVLTLLEHPDQLRRLREDPALIQGAVEELLRFVPLG

VGAAQARYATEDIEVGGTLVRSGEPVLVAVGSANRDALRFDEPGVLNVA

RPTTQHLGFGHGVHHCLGAPLARLELQEALGALITRFPGLRLAGDIEWK

DRMLVRGPRVMPIGW
```

Amino acid sequences SEQ ID Nos. 1 and 2 are preferable encoded by nucleic acid sequences SEQ ID Nos. 3 and 4, with nucleic acid sequences SEQ ID Nos. 5 and 6 being optimized for expression in *E. coli*.

```
SEQ ID No. 3:
ATGTTGACCACAGCCGAGACGACATCCATCGCCTATCCCTTCAACACCGC

CGAAGGGCTGGCGCTCAGCGAGCGTTACGAAGAGGCCAGGAACCGCACCG

GACTGCTCCGGGTGCGGATGCCCTACGGTGAGCCCGCCTGGCTGGTCACG

CGGTACGCCGACGCCCGGCTGGTGCTCGGCGACCGGCGCTTCAGCCGTGC

GGAGGCGCTCCACCACGACGAGCCGCGGCAGTCCGAAGGCCGGCGCGACA

GCGGCATCCTGACCATGGACCCGCCCGACCACACCCGGCTGCGCACCCTC

GTCGCCAAGGCGTTCACCGTCCACCAGGTGGAGAAACTCCGCCCCTGGGT

ACGCCAGTTGACCCATGACCTGCTCGACGACCTCGAGGCCGCCGGGCCGC

CCGCCGATCTGGTGGACCGCTACGCCCTGCCCATTCCGGTCGGCGTCATC

TGCGCCATGCTCGGCGTCCCGCAGGAGGACCGGCCCAAGTTCCGGGTCTG

GAGCGACGCCGCGCTGTCCACCAGCTCGCTGAGCGCCGAGCAGTTCGCCC

GTAACACCGACGAGCTGCGCGCCTACATGGCCGGGCTGATCGAGGACCAC

CGCAGGACCCCGCGGGACGACATCATGACCTCGCTGATCGAGGCGCGGGA

CGCGGGCGACCGGCTGTCCGAGCTGGAACTCGTCGATCTGTGCGTGGGCA

TCCTGGTGGCCGGGCACGAGACCACCGCCACCCAGATCCCCAACTTCGTG

CTGACGCTGCTGGAGCACCCGGACCAGCTGCGCCGGCTGCGCGAGGACCC

CGCCCTGATCCAGGGCGCCGTCGAGGAGCTGCTGCGCTTCGTCCCGCTGG

GCGTGGGCGCCGCCCAGGCCCGTTACGCCACCGAGGACATCGAGGTGGGC

GGCACGCTGGTGCGCAGCGGGGAGCCGGTGCTGGTCGCCGTCGGCTCGGC

CAACCGCGACGCGCTGCGCTTCGACGAACCGGGCGTGCTCAACGTCGCCC

GCCCCACCACCCAGCACCTCGGCTTCGGCCACGGTGTGCACCACTGCCTG

GGCGCGCCCCTGGCCCGTCTGGAGCTCCAGGAGGCGCTCGGCGCGCTGAT

CACGCGCTTCCCGGGCCTGCGGCTGGCCGGGGACATCGAGTGGAAGGACC

GCATGCTGGTCCGCGGGCCCCGTGTCATGCCCATCGGGTGGTGA

SEQ ID No. 4:
ATGCCCTACGGTGAGCCCGCCTGGCTGGTCACGCGGTACGCCGACGCCCG

GCTGGTGCTCGGCGACCGGCGCTTCAGCCGTGCGGAGGCGCTCCACCACG

ACGAGCCGCGGCAGTCCGAAGGCCGGCGCGACAGCGGCATCCTGACCATG

GACCCGCCCGACCACACCCGGCTGCGCACCCTCGTCGCCAAGGCGTTCAC

CGTCCACCAGGTGGAGAAACTCCGCCCCTGGGTACGCCAGTTGACCCATG

ACCTGCTCGACGACCTCGAGGCCGCCGGGCCGCCCGCCGATCTGGTGGAC

CGCTACGCCCTGCCCATTCCGGTCGGCGTCATCTGCGCCATGCTCGGCGT

CCCGCAGGAGGACCGGCCCAAGTTCCGGGTCTGGAGCGACGCCGCGCTGT

CCACCAGCTCGCTGAGCGCCGAGCAGTTCGCCCGTAACACCGACGAGCTG

CGCGCCTACATGGCCGGGCTGATCGAGGACCACCGCAGGACCCCGCGGGA

CGACATCATGACCTCGCTGATCGAGGCGCGGGACGCGGGCGACCGGCTGT

CCGAGCTGGAACTCGTCGATCTGTGCGTGGGCATCCTGGTGGCCGGGCAC

GAGACCACCGCCACCCAGATCCCCAACTTCGTGCTGACGCTGCTGGAGCA

CCCGGACCAGCTGCGCCGGCTGCGCGAGGACCCCGCCCTGATCCAGGGCG

CCGTCGAGGAGCTGCTGCGCTTCGTCCCGCTGGGCGTGGGCGCCGCCCAG

GCCCGTTACGCCACCGAGGACATCGAGGTGGGCGGCACGCTGGTGCGCAG

CGGGGAGCCGGTGCTGGTCGCCGTCGGCTCGGCCAACCGCGACGCGCTGC

GCTTCGACGAACCGGGCGTGCTCAACGTCGCCCGCCCCACCACCCAGCAC

CTCGGCTTCGGCCACGGTGTGCACCACTGCCTGGGCGCGCCCCTGGCCCG

TCTGGAGCTCCAGGAGGCGCTCGGCGCGCTGATCACGCGCTTCCCGGGCC
```

-continued

TGCGGCTGGCCGGGGACATCGAGTGGAAGGACCGCATGCTGGTCCGCGGG

CCCCGTGTCATGCCCATCGGGTGGTGA

SEQ ID No. 5:
ATGCTGACCACCGCAGAAACCACCAGTATTGCATATCCGTTTAATACCGC

AGAAGGTCTGGCACTGAGCGAACGTTATGAAGAAGCACGTAATCGTACCG

GTCTGCTGCGTGTTCGTATGCCGTATGGTGAACCGGCATGGCTGGTTACC

CGTTATGCAGATGCCCGTCTGGTTCTGGGTGATCGTCGTTTTAGCCGTGC

CGAAGCACTGCATCACGATGAACCGCGTCAGAGCGAAGGTCGTCGTGATA

GCGGTATTCTGACCATGGATCCGCCTGATCATACCCGTCTGCGTACCCTG

GTTGCAAAAGCATTTACCGTTCATCAGGTTGAAAAACTGCGTCCGTGGGT

TCGCCAGCTGACCCATGATCTGCTGGATGATCTGGAAGCAGCAGGTCCGC

CTGCAGATCTGGTTGATCGTTATGCACTGCCGATTCCGGTTGGTGTTATT

TGTGCAATGCTGGGTGTTCCGCAAGAAGATCGTCCTAAATTTCGTGTTTG

GAGTGATGCAGCACTGAGCACCAGCAGCCTGAGCGCAGAACAGTTTGCAC

GTAATACCGATGAACTGCGTGCATATATGGCAGGTCTGATTGAAGATCAT

CGTCGTACACCGCGTGATGATATTATGACCAGCCTGATCGAAGCACGTGA

TGCCGGTGATCGCCTGAGTGAACTGGAACTGGTGGATCTGTGTGTTGGTA

TTCTGGTTGCAGGTCATGAAACCACCGCAACCCAGATTCCGAATTTTGTT

CTGACCCTGCTGGAACATCCGGATCAGCTGCGTCGTCTGCGTGAAGATCC

GGCACTGATTCAGGGTGCAGTTGAAGAACTGCTGCGTTTTGTTCCGCTGG

GTGTGGGTGCAGCACAGGCACGTTATGCAACCGAAGATATTGAAGTTGGT

GGCACCCTGGTTCGTAGTGGCGAACCGGTGCTGGTTGCCGTTGGTAGCGC

AAACCGTGATGCACTGCGCTTTGATGAACGGGTGTTCTGAATGTTGCAC

GTCCGACCACACAGCATCTGGGTTTTGGTCATGGTGTTCATCATTGTCTG

GGTGCACCGCTGGCACGTCTGGAACTGCAAGAAGCACTGGGAGCACTGAT

TACCCGTTTTCCGGGTCTGCGTCTGGCAGGCGATATTGAATGGAAAGATC

GTATGCTGGTTCGTGGTCCGCGTGTTATGCCGATTGGTTGGTAA

SEQ ID No. 6:
ATGGTGAACCGGCATGGCTGGTTACCCGTTATGCAGATGCCCGTCTGGTT

CTGGGTGATCGTCGTTTTAGCCGTGCCGAAGCACTGCATCACGATGAACC

GCGTCAGAGCGAAGGTCGTCGTGATAGCGGTATTCTGACCATGGATCCGC

CTGATCATACCCGTCTGCGTACCCTGGTTGCAAAAGCATTTACCGTTCAT

CAGGTTGAAAAACTGCGTCCGTGGGTTCGCCAGCTGACCCATGATCTGCT

GGATGATCTGGAAGCAGCAGGTCCGCCTGCAGATCTGGTTGATCGTTATG

CACTGCCGATTCCGGTTGGTGTTATTTGTGCAATGCTGGGTGTTCCGCAA

GAAGATCGTCCTAAATTTCGTGTTTGGAGTGATGCAGCACTGAGCACCAG

CAGCCTGAGCGCAGAACAGTTTGCACGTAATACCGATGAACTGCGTGCAT

ATATGGCAGGTCTGATTGAAGATCATCGTCGTACACCGCGTGATGATATT

ATGACCAGCCTGATCGAAGCACGTGATGCCGGTGATCGCCTGAGTGAACT

GGAACTGGTGGATCTGTGTGTTGGTATTCTGGTTGCAGGTCATGAAACCA

CCGCAACCCAGATTCCGAATTTTGTTCTGACCCTGCTGGAACATCCGGAT

CAGCTGCGTCGTCTGCGTGAAGATCCGGCACTGATTCAGGGTGCAGTTGA

AGAACTGCTGCGTTTTGTTCCGCTGGGTGTGGGTGCAGCACAGGCACGTT

ATGCAACCGAAGATATTGAAGTTGGTGGCACCCTGGTTCGTAGTGGCGAA

CCGGTGCTGGTTGCCGTTGGTAGCGCAAACCGTGATGCACTGCGCTTTGA

TGAACGGGTGTTCTGAATGTTGCACGTCCGACCACACAGCATCTGGGTT

TTGGTCATGGTGTTCATCATTGTCTGGGTGCACCGCTGGCACGTCTGGAA

CTGCAAGAAGCACTGGGAGCACTGATTACCCGTTTTCCGGGTCTGCGTCT

GGCAGGCGATATTGAATGGAAAGATCGTATGCTGGTTCGTGGTCCGCGTG

TTATGCCGATTGGTTGGTAA

"Identical" as used herein means that two or more amino acid sequences, when superimposed on one another, may have a certain "identity" (matching amino acid residues at identical positions) to one another. "Identity" is defined in this invention as the percentage of amino acids of eligible amino acid sequences that are identical to the amino acids of the starting sequence, namely after the alignment of the two sequences and the introduction of gaps, if necessary, in order to achieve the maximum percentual sequence identity as generated by the "protein BLAST" program (blastp; Altschul et al., J. Mol. Biol. (1997) 215:403-410; http://blast.ncbi.nlm.nih.gov/Blast.cgi; commonly referred to herein as "BLAST"), with all variable parameters set to default values. Herein, the algorithm "blastp (protein-protein-BLAST)" is used with the following parameters: "expect threshold": 0.05; "word size": 6; matrix: BLOSUM62; "gap costs": "Existence" 11, "Extension" 1; conditional compositional score matrix adjustment; no filter and no mask. A percentage (%) value for the amino acid sequence identity is determined by the number of matching identical nucleotides divided by the sequence length for which the identity in percent is recorded.

A further aspect of the present invention relates to a method of preparing a steroid or a derivative thereof having the general formula (II)

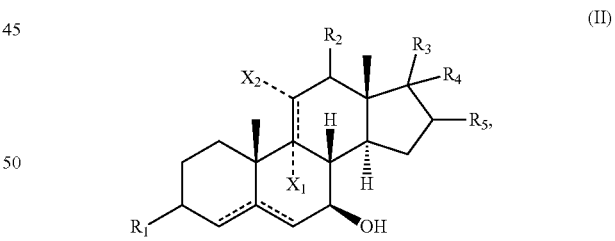

(II)

wherein
X$_1$ and X$_2$ are independently H, Cl, F, Br, I, CF$_3$, a C$_1$ to C$_6$ alkyl radical, OH, a C$_1$ to C$_6$ alkoxy radical, CN, NO$_2$, N(R$_6$)$_2$, an epoxy group, CHO or a CO$_2$R$_6$ radical, wherein
R$_6$ is —C(O)H, —C(O)CH$_3$, —C(O)CH$_2$CH$_3$, —C(O)(CH$_2$)$_2$CH$_3$, —C(O)CH(CH$_3$)$_2$, —C(O)(CH$_2$)$_3$CH$_3$, —C(O)CH(CH$_3$)CH$_2$CH$_3$, —C(O)CH$_2$CH$_2$(CH$_3$)$_2$, —C(O)C(CH$_3$)$_3$, —C(O)Ph, —C(O)CH$_2$Ph,
R$_1$ and R$_2$ are independently H, OH, OR$_7$ or O, wherein
R$_7$ is —C(O)H, —C(O)CH$_3$, —C(O)CH$_2$CH$_3$, —C(O)(CH$_2$)$_2$CH$_3$, —C(O)CH(CH$_3$)$_2$, —C(O)

(CH$_2$)$_3$CH$_3$, —C(O)CH(CH$_3$)CH$_2$CH$_3$, —C(O)CH$_2$CH$_2$(CH$_3$)$_2$, —C(O)C(CH$_3$)$_3$, —C(O)Ph, —C(O)CH$_2$Ph,

R$_3$ is H, OH, OR$_8$, a C$_1$ to C$_{10}$ alkyl radical, a C$_1$ to C$_{10}$ alkenyl radical, —CHO, —C(O)(CH$_3$), —C(O)(CH$_2$OH)), —CH(CH$_3$)C(O)C$_{13}$, —CH(CH$_3$)((CH$_2$)$_2$CO$_2$R$_9$) or —CH(CH$_3$)((CH$_2$)$_2$CONHR$_9$), wherein R$_8$ is —C(O)H, —C(O)CH$_3$, —C(O)CH$_2$CH$_3$, —C(O)(CH$_2$)$_2$CH$_3$, —C(O)CH(CH$_3$)$_2$, —C(O)(CH$_2$)$_3$CH$_3$, —C(O)CH(CH$_3$)CH$_2$CH$_3$, —C(O)CH$_2$CH$_2$(CH$_3$)$_2$, —C(O)C(CH$_3$)$_3$, —C(O)Ph or —C(O)CH$_2$Ph, and R$_9$ is —CH$_3$, —CH$_2$COOH, —CH$_2$CH$_3$, —CH(CH$_3$)$_2$, —(CH$_2$)$_2$CH$_3$, —(CH$_2$)$_2$SO3H, C(CH$_3$)$_3$, —(CH$_2$)$_3$CH$_3$, —CH(CH$_3$)CH$_2$CH$_3$, —CH$_2$CH$_2$(CH$_3$)$_2$, an aryl group or an alkylaryl group, R$_4$ is H, OH, or —OR$_{10}$, wherein R$_{10}$ is —C(O)H, —C(O)CH$_3$, —C(O)CH$_2$CH$_3$, —C(O)(CH$_2$)$_2$CH$_3$, —C(O)CH(CH$_3$)$_2$, —C(O)(CH$_2$)$_3$C$_1$-3, —C(O)CH(CH$_3$)CH$_2$CH$_3$, —C(O)CH$_2$CH$_2$(CH$_3$)$_2$, —C(O)C(CH$_3$)$_3$, —C(O)Ph or —C(O)CH$_2$Ph, and R$_5$ is H, CF$_3$, a C$_1$ to C$_6$ alkyl radical, a C$_1$ to C$_6$ alkenyl radical, OH, O, or a C$_1$ to C$_6$ alkoxy radical, wherein the dashed line denotes an optional double bond, with the proviso that the B ring has no double bond if the A ring has a C$_4$-C$_5$ double bond, and the C ring has no double bond if X$_1$ and X$_2$ form an epoxy group, comprising the step of converting a 7-deoxysteroid or a derivative thereof having the general formula (I)

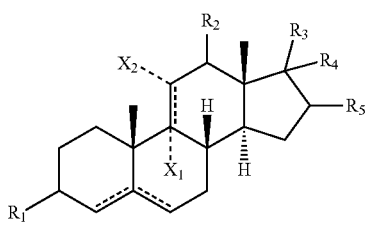

(I)

with cytochrome P450 or a functional variant thereof, characterized in that the cytochrome P450 enzyme comprises an amino acid sequence which is at least 80%, preferably at least 90%, in particular 100%, identical to the amino acid sequence SEQ ID No. 1 or 2.

Using the method according to the invention, 7-deoxysteroids or, respectively, derivatives thereof having the general formula (I) can be converted with cytochrome P450 according to the invention or a functional variant thereof to steroids or, respectively, derivatives thereof having the general formula (II).

In order to support the redox reaction of cytochrome P450 according to the invention or, respectively, its functional variants thereof, it is advantageous to carry out the method according to the invention in the presence of a reducing agent. NAD(P)H, flavins or ferredoxins can be used as reducing agents. For example, if the redox cofactors NAD(P)+ and/or NAD(P)H are used, it is advantageous to use them at a concentration of 0.001 mM and 10 mM, more preferably between 0.05 mM and 1 mM, in a reaction mixture.

The method according to the invention is preferably carried out in the presence of redox partners for cytochrome P450. Redox partners are understood to be proteins of the ferredoxin and ferredoxin reductase classes, which are advantageous for the function of cytochrome P450 according to the present invention. A possible pair of redox partners preferably comprises putidaredoxin and putidaredoxin reductase from *Pseudomonas putida*. Moreover, a person skilled in the art is able to identify further ferredoxin proteins and ferredoxin reductases which are potential redox partners for the cytochrome P450 according to the invention. Suitability as a redox partner can be verified in a functional assay, as described, for example, in Examples 3 to 5. The putidaredoxin used in these examples and/or the putidaredoxin reductase used therein can be replaced by possible alternative proteins or enzymes, respectively. If sufficient formation of the desired product (e.g., ursocholic acid) is observed, the tested redox partners can be regarded as functional alternatives to putidaredoxin and/or putidaredoxin reductase.

According to a particularly preferred embodiment of the present invention, the ferredoxin used in the method according to the invention comprises an amino acid sequence which is at least 80%, preferably at least 85%, more preferably at least 90%, more preferably at least 95%, more preferably at least 96%, more preferably at least 97%, more preferably at least 98%, more preferably at least 99%, in particular 100%, identical to the amino acid sequence SEQ ID No. 7, wherein X is a methionine residue or is not an amino acid.

SEQ ID No. 7:
XSKVVYVSHDGTRRELDVADGVSLMQAAVSNGIYDIVGDCGGSASCAT

CHVYVNEAFTDKVPAANEREIGMLECVTAELKPNSRLCCQIIMTPELD

GIVVDVPDRQW

According to a further preferred embodiment of the present invention, the ferredoxin reductase used in the method according to the invention comprises an amino acid sequence which is at least 80%, preferably at least 85%, more preferably at least 90%, more preferably at least 95%, more preferably at least 96%, more preferably at least 97%, more preferably at least 98%, more preferably at least 99%, in particular 100%, identical to the amino acid sequence SEQ ID No. 8.

SEQ ID No. 8:
MNANDNVVIVGTGLAGVEVAFGLRASGWEGNIRLVGDATVIPHHLPPL

SKAYLAGKATAESLYLRTPDAYAAQNIQLLGGTQVTAINRDRQQVILS

DGRALDYDRLVLATGGRPRPLPVASGAVGKANNFRYLRTLEDAECIRR

QLIADNRLVVIGGGYIGLEVAATAIKANMHVTLLDTAARVLERVTAPP

VSAFYEHLHREAGVDIRTGTQVCGFEMSTDQQKVTAVLCEDGTRLPAD

LVIAGIGLIPNCELASAAGLQVDNGIVINEHMQTSDPLIMAVGDCARF

HSQLYDRWVRIESVPNALEQARKIAAILCGKVPRDEAAPWFWSDQYEI

GLKMVGLSEGYDRIIVRGSLAQPDFSVFYLQGDRVLAVDTVNRPVEFN

QSKQIITDRLPVEPNLLGDESVPLKEIIAAAKAELSSA

Amino acid sequences SEQ ID Nos. 7 and 8 are preferably encoded by nucleic acid sequences SEQ ID Nos. 9 and 10, respectively, with nucleic acid sequences SEQ ID Nos. 11 and 12 being optimized for expression in *E. coli*.

SEQ ID No. 9:
(ATG)$_{0 \text{ or } 1}$
TCTAAAGTAGTGTATGTGTCACATGATGGAACGCGTCGCGAACTGGATG
TGGCGGATGGCGTCAGCCTGATGCAGGCTGCAGTCTCCAATGGTATCTA
CGATATTGTCGGTGATTGTGGCGGCAGCGCCAGCTGTGCCACCTGCCAT
GTCTATGTGAACGAAGCGTTCACGGACAAGGTGCCCGCCGCCAACGAGC
GGGAAATCGGCATGCTGGAGTGCGTCACGGCCGAACTGAAGCCGAACAG
CAGGCTCTGCTGCCAGATCATCATGACGCCCGAGCTGGATGGCATCGTG
GTCGATGTTCCCGATAGGCAATGGTAA SEQ ID No. 10:
ATGAACGCAAACGACAACGTGGTCATCGTCGGTACCGGACTGGCTGGCG
TTGAGGTCGCCTTCGGCCTGCGCGCCAGCGGCTGGGAAGGCAATATCCG
GTTGGTGGGGGATGCGACGGTAATTCCCCATCACCTACCACCGCTATCC
AAAGCTTACTTGGCCGGCAAAGCCACAGCGGAAAGCCTGTACCTGAGAA
CCCCAGATGCCTATGCAGCGCAGAACATCCAACTACTCGGAGGCACACA
GGTAACGGCTATCAACCGCGACCGACAGCAAGTAATCCTATCGGATGGC
CGGGCACTGGATTACGACCGGCTGGTATTGGCTACCGGAGGGCGTCCAA
GACCCCTACCGGTGGCCAGTGGCGCAGTTGGAAAGGCGAACAACTTTCG
ATACCTGCGCACACTCGAGGACGCCGAGTGCATTCGCCGGCAGCTGATT
GCGGATAACCGTCTGGTGGTGATTGGTGGCGGCTACATTGGCCTTGAAG
TGGCTGCCACCGCCATCAAGGCGAACATGCACGTCACCCTGCTTGATAC
GGCAGCCCGGGTTCTGGAGCGGGTTACCGCCCCGCCGGTATCGGCCTTT
TACGAGCACCTACACCGCGAAGCCGGCGTTGACATACGAACCGGCACGC
AGGTGTGCGGGTTCGAGATGTCGACCGACCAACAGAAGGTTACTGCCGT
CCTCTGCGAGGACGGCACAAGGCTGCCAGCGGATCTGGTAATCGCCGGG
ATTGGCCTGATACCAAACTGCGAGTTGGCCAGTGCGGCCGGCCTGCAGG
TTGATAACGGCATCGTGATCAACGAACACATGCAGACCTCTGATCCCTT
GATCATGGCCGTCGGCGACTGTGCCCGATTTCACAGTCAGCTCTATGAC
CGCTGGGTGCGTATCGAATCGGTGCCCAATGCCTTGGAGCAGGCACGAA
AGATCGCCGCCATCCTCTGTGGCAAGGTGCCACGCGATGAGGCGGCGCC
CTGGTTCTGGTCCGATCAGTATGAGATCGGATTGAAGATGGTCGGACTG
TCCGAAGGGTACGACCGGATCATTGTCCGCGGCTCTTTGGCGCAACCCG
ACTTCAGCGTTTTCTACCTGCAGGGAGACCGGGTATTGGCGGTCGATAC
AGTGAACCGTCCAGTGGAGTTCAACCAGTCAAAACAAATAATCACGGAT
CGTTTGCCGGTTGAACCAAACCTACTCGGTGACGAAAGCGTGCCGTTAA
AGGAAATCATCGCCGCCGCCAAAGCTGAACTGAGTAGTGCCTGA SEQ ID No. 11:
(ATG)$_{0 \text{ or } 1}$
ATGAGCAAAGTGGTCTATGTGTCGCATGATGGAACACGCCGTGAGTTAG
ACGTCGCTGATGGTGTATCCCTGATGCAAGCAGCGGTTAGCAATGGCAT
TTACGACATCGTTGGCGATTGTGGTGGTAGTGCGTCATGTGCAACGTGT CACGTGTATGTTAACGAAGCGTTTACCGATAAGGTGCCTGCTGCCAATG
AACGCGAGATTGGCATGCTGGAATGCGTAACTGCCGAACTCAAACCGAA
CTCTCGCCTGTGCTGCCAGATCATCATGACCCCGGAATTGGACGGGATT
GTCGTTGATGTGCCAGATCGTCAGTGGTAA SEQ ID No. 12:
ATGAACGCCAATGATAATGTTGTTATTGTTGGCACCGGTCTGGCAGGCG
TTGAAGTTGCATTTGGTCTGCGTGCAAGCGGTTGGGAAGGTAATATTCG
TCTGGTTGGTGATGCAACCGTTATTCCGCATCATCTGCCTCCGCTGAGC
AAAGCATATCTGGCAGGTAAAGCAACCGCAGAAAGCCTGTATCTGCGTA
CACCGGATGCCTATGCAGCACAGAATATTCAGCTGCTGGGTGGTACACA
GGTTACCGCAATTAATCGTGATCGTCAGCAGGTTATTCTGAGTGATGGT
CGTGCACTGGATTATGATCGTCTGGTGCTGGCAACCGGTGGTCGTCCGC
GTCCGCTGCCCGGTTGCAAGTGGTGCAGTTGGTAAAGCCAATAACTTTCG
TTATCTGCGCACCCTGGAAGATGCAGAATGTATTCGTCGTCAGCTGATT
GCAGATAATCGCCTGGTTGTGATTGGTGGTGGTTATATTGGTCTGGAAG
TTGCAGCAACCGCCATTAAAGCAAATATGCATGTTACCCTGCTGGATAC
CGCAGCACGTGTTCTGGAACGTGTTACCGCACCGCCTGTTAGCGCCTTT
TATGAACATCTGCATCGTGAAGCCGGTGTTCATATTCGTACCGGCACCC
AGGTTTGTGGTTTTGAAATGAGCACCGATCAGCAGAAAGTTACCGCAGT
TCTGTGTGAAGATGGCACCCGTCTGCCTGCAGATCTGGTTATTGCAGGT
ATTGGCCTGATTCCGAATTGTGAACTGGCAAGCGCAGCAGGTCTGGCAG
TTGGTGATTGTGCACGTTTTCATAGCCAGCTGTATGATCGTTGGGTTCG
TATTGAAAGCGTTCCGAATGCACTGGAACAGGCACGTAAAATTGCAGCA
ATTCTGTGTGGTAAAGTTCCGCGTGATGAAGCAGCACCGTGGTTTTGGA
GCGATCAGTATGAAATTGGTCTGAAAATGGTTGGTCTGAGCGAAGGTTA
TGATCGCATTATTGTTCGTGGTAGCCTGGCACAGCCGGATTTTTCAGTT
TTTTATCTGCAGGGTGATCGTGTGCTGGCAGTTGATACCGTTAATCGTC
CGGTTGAATTTAACCAGAGCAAACAAATTATCACCGATCGTCTGCCGGT
GGAACCGAATCTGCTGGGAGATGAAAGCGTGCCGCTGAAAGAAATTATT
GCAGCAGCAAAAGCAGAACTGAGCAGCGCATAA The expression of the cytochrome P450 according to the invention and any ferredoxins and ferredoxin reductases in bacteria, in particular in *E. coli*, is particularly advantageous when nucleic acids with the nucleic acid sequences SEQ ID No. 5, SEQ ID No. 6, SEQ ID No. 11 and/or SEQ ID No. 12 are used. Further aspects of the present invention therefore relate to a nucleic acid (DNA and/or RNA) with a nucleic acid sequence selected from the group consisting of SEQ ID No. 5, SEQ ID No. 6, SEQ ID No. 11 and SEQ ID No. 12 and vectors and/or cells, in particular *E. coli* cells, comprising at least one of those sequences.

It has been shown that it is particularly advantageous if the above-mentioned ferredoxins and ferredoxin reductases are expressed (co-expressed) together with cytochrome P450 in a production strain (e.g., an *E. coli* strain). Through the co-expression of the three proteins or, respectively, enzymes, ideally under the same promoter, an ideal balance between the enzymes can be established, which has a particularly advantageous effect on the enzymatic conversion of a substrate.

According to a preferred embodiment of the present invention, the method according to the invention is performed at a temperature of from 10° to 40° C., preferably from 15° to 38° C., more preferably from 20° C. to 30° C., more preferably from 22° C. to 26° C. It has been shown according to the invention that the enzyme activity of cytochrome P450 for the reaction according to the invention is particularly high in this area.

According to a further preferred embodiment of the present invention, the method according to the invention is performed at a pH of from 6.5 to 8.5, preferably from 7 to 8, more preferably from 7.2 to 7.8. At this pH value, the enzyme activity of cytochrome P450 is highest so as to allow an appropriate conversion of the substrate.

The hydroxylation of deoxysteroids or, respectively, deoxysteroid derivatives can be carried out regioselectively at position 7 of the steroid backbone. In this way, in particular, a 7beta-hydroxyl group can be introduced stereoselectively so that, for example, ursocholic acid and/or ursocholic acid derivatives can be produced.

In the method according to the present invention, the isolation of the product can be effected in different ways. For example, the product can be extracted from the reaction mixture by a suitable organic solvent. Depending on the substrate, such solvents are described in the literature. According to the present invention, cholic acids and their derivatives can be isolated from reaction mixtures, for example, with ethyl acetate, optionally after acidification of the reaction mixture, e.g., with HCl. A method in which bile acids are present in the form of a salt, e.g., a sodium salt, in an aqueous solution constitutes a special case. In this case, a precipitation of the product can be effected by acidifying the reaction mixture. For this purpose, for example, HCl or dilute HCl can be added to the reaction mixture in a sufficient amount. If a pH value of, for example, 1 to 4, preferably 2 to 3, is achieved in the process, the product predominantly exists in the form of a suspension. The product can then be removed from the reaction mixture by common methods such as, e.g., filtration or centrifugation. Chromatographic methods, such as, e.g., column chromatography or flash chromatography, are another alternative that can be used for product isolation, for example. Furthermore, it is possible, for example, to obtain product by evaporating the reaction solvent.

Alternatively, in a method according to the present invention, the product(s) may also remain in the reaction mixture after the reaction, e.g., in order to carry out even more reactions and optionally isolate an end product upon completion of those reactions. It is also conceivable that the substrate(s) for the method according to the present invention is/are produced in the same reaction batch by previous reactions or reactions taking place in parallel.

EXAMPLES

The present invention is explained in further detail using the following examples, without, however, being restricted thereto.

Example 1: Test of Bacterial Strains

The following bacterial strains were obtained from the German Strain Collection of Microorganisms and Cell Cultures (DSMZ [Deutsche Stammsammlung für Mikroorganismen und Zellkulturen]): *Saccharothrix longispora* (DSM-43749), *Catellatospora citrae* (DSM-44097), *Streptomyces hygroscopicus* subsp. *hygroscopicus* (DSM-40578) and *Asanoa ferruginea* (DSM-44099). The strains were cultivated under standard conditions as recommended by DSMZ. As soon as the growth of the cultures had led to visible turbidity, deoxycholic acid (0.5 mM) was added, and it was cultured further for up to 72 h. After a centrifugation step, supernatants of the cultures were extracted with ethyl acetate and analyzed by HPLC and GC/MS. In the HPLC chromatogram of the reaction with *Streptomyces hygroscopicus*, a peak was noted the retention time of which corresponds to that of ursocholic acid. The GC/MS analysis indicated that the potential ursocholic acid peak originates from a bile acid with 3 hydroxyl groups. The examination of the other strains gave no indication of 7-hydroxylated products of deoxycholic acid.

Example 2: Genome Sequencing and Annotation of the P450 Genes

Upon cultivation of *Streptomyces hygroscopicus* subsp. *hygroscopicus* (DSM-40578) according to the DSMZ regulation, the genomic DNA of the strain was isolated (Kieser et al. (2000), Practical *Streptomyces* genetics (Norwich: John Innes Foundation)). The genome was sequenced using Illumina MiSeq, and an assembly based on the known genome of *Streptomyces rapamycinicus* was conducted (Microsynth GmbH, Switzerland). 42 P450 genes could be identified by homology comparisons.

Example 3: Cloning of Expression System

Using the restriction enzyme XhoI, the following construct comprising coding regions for putidaredoxin reductase (PtR) and putidaredoxin (Ptx) was cloned into plasmid pJ411 (DNA 2.0).

Synthetic DNA (Life Technologies): 5', XhoI interface, HindIII interface, approx. 50 bp spacer DNA, ribosome binding site (rbs), ORF (open reading frame) putidaredoxin reductase (PtR), approx. 50 bp spacer DNA, rbs, ORF putidaredoxin (Ptx), XhoI interface, 3'.

The result of the cloning step was checked by means of restriction enzyme digestion and DNA sequencing.

Subsequently, using the restriction enzymes NdeI and HindIII, one ORF each coding for the P450 hydroxylases identified in Example 2 was cloned into the above-mentioned synthetic DNA or plasmid, respectively (Life Technologies). The result was again verified by means of restriction enzyme digestion and DNA sequencing. The expression vector used in this example and the redox partners used constitute only one way of expressing the cytochrome P450 enzymes according to the invention, which way has been chosen as an example.

The expression plasmids produced with the identified P450 candidates (see example 2) can be used for jointly expressing the respective P450 proteins together with putidaredoxin reductase and putidaredoxin. The 3 ORFs of the respective expression plasmids are expressed under the control of a T7 promoter on a common mRNA, but as separate polypeptides.

Example 4: Expression of P450/Ptx/PtR

After the genome sequencing of *Streptomyces hygroscopicus* subsp. *hygroscopicus*, there were 42 P450 sequences that came into consideration as candidates for a possible deoxycholic acid-7-hydroxylase. To identify the enzyme looked for, ORFs of the candidates were cloned into the expression system described in example 3 and into a pJ411 (DNA 2.0) expression vector without coding regions for putidaredoxin reductase (PtR) and putidaredoxin (Ptx). The following protocol was used for the expression.

TB-P450 Expression Medium:
 Terrific broth (TB) medium
 +50 µg/ml kanamycin
 +0.5 mM 5-aminolevulinic acid (from 100× parent solution)
 +1 mM thiamine (from 100× parent solution)
 +1 mM $MgCl_2$+2.5 mM ammonium sulfate+50 µM $FeCl_3$ (from 100× parent solution)
 +0.5 mM IPTG (from 1 M parent solution)
 (the additives were each 0.2 µm sterile filtered)

P450 Lysis Buffer:
 100 mM Tris pH 7.5
 20% (v/v) glycerin
 1 mg/ml lysozyme

The constructs of the P450 candidates, which were to be tested, were transformed into the *E. coli* expression strain BL21 (DE3). Overnight cultures were inoculated from single colonies (LB (lysogeny broth)+kanamycin). The next day, 1:100 expression cultures were inoculated therewith (150 ml TB (terrific broth)-P450 expression medium) and were initially shaken at 370° C. in baffled flasks (1 L) for 3 h. Subsequently, the temperature was lowered to 240° C., and it was shaken for another 22 h. The cultures were harvested by centrifugation at 5000 g for 10 min, washed 1× with 0.9% (w/v) NaCl, and pellets were frozen at −80° C. The cell pellets were thawed, weighed and resuspended with an equivalent amount of P450 lysis buffer, incubated on ice for 1 h and then digested using a sonifier. Upon centrifugation (30 min, 21000 g), the supernatants were used for test reactions.

Example 5: Testing of P450 Candidates for DA Hydroxylation

Reaction Mixture:
 10-80 µl 100 mM NADH (redox cofactor)
 250 µl 1 M Tris-HCl pH 7.5
 17.5 µl glycerin (50%)
 100 µl 50 mM deoxycholic acid solution pH 8.5 (final 10 mM)
 50 µl *E. coli* lysate P450/PtR/Ptx (see Example 4)
 17.5-87.5 µl $dH_2O$ The reactions were set up in 1.5 ml screw-top bottles and sealed with lids with aluminium foil. The foil was punctured in several places. It was gently shaken at 24° C. for 18 h. 200 µl of the reaction batch was diluted with 600 µl acetonitrile/5 µl $H_3PO_4$ (50%) and incubated at 550° C. for 15 minutes. Subsequently, the samples were centrifuged at 20817 rcf for 5 minutes and analyzed using HPLC/DAD (e.g., Agilent 1200 series;
 column: Merck Purospher STAR RP-18e 125×4 mm, 5 µm;
 flow rate: 1.5 ml/min, gradient $H_2O$+$H_3PO_4$ (pH=2.6)/acetonitrile). One of the examined candidates ("P450_c866") was able to hydroxylate deoxycholic acid to ursocholic acid. The deoxycholic acid used was converted in the process (see the following table). The identity of the product ursocholic acid was verified by GC/MS analysis and by 2D NMR.

| Redox cofactor [µl] | ursocholic acid [µg/ml] | conversion [%] |
|---|---|---|
| 10 | 30 | 3.4 |
| 30 | 48 | 5.3 |
| 50 | 57 | 6.2 |
| 80 | 110 | 11.6 |

In this example, a redox cofactor (NADH) is oxidized by the P450/Ptx/PtR reaction.

The invention claimed is:

1. A method of preparing a steroid having the general formula (II):

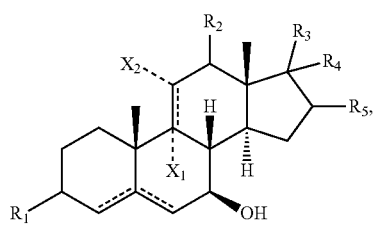

(II)

wherein $X_1$ and $X_2$ are independently H, Cl, F, Br, I, $CF_3$, a $C_1$ to $C_6$ alkyl radical, OH, a $C_1$ to $C_6$ alkoxy radical, CN, $NO_2$, $N(R_6)_2$, an epoxy group, CHO, or a $CO_2R_6$ radical, wherein
$R_6$ is —C(O)H, —C(O)$CH_3$, —C(O)$CH_2CH_3$, —C(O)($CH_2$)$_2CH_3$, —C(O)CH($CH_3$)$_2$, —C(O)($CH_2$)$_3CH_3$, —C(O)CH($CH_3$)$CH_2CH_3$, —C(O)$CH_2CH_2$($CH_3$)$_2$, —C(O)C($CH_3$)$_3$, —C(O)Ph, or —C(O)$CH_2$Ph, $R_1$ and $R_2$ are independently H, OH, $OR_7$, or O, wherein
$R_7$ is —C(O)H, —C(O)$CH_3$, —C(O)$CH_2CH_3$, —C(O)($CH_2$)$_2CH_3$, —C(O)CH($CH_3$)$_2$, —C(O)($CH_2$)$_3CH_3$, —C(O)CH($CH_3$)$CH_2CH_3$, —C(O)$CH_2CH_2$($CH_3$)$_2$, —C(O)C($CH_3$)$_3$, —C(O)Ph, or —C(O)$CH_2$Ph, $R_3$ is H, OH, $OR_8$, a $C_1$ to $C_{10}$ alkyl radical, a $C_1$ to $C_{10}$ alkenyl radical, —CHO, —C(O)(CH$_3$), —C(O)(CH$_2$OH), —CH(CH$_3$)C(O)CH$_3$, —CH(CH$_3$)((CH$_2$)$_2$CO$_2$R$_9$), or —CH(CH$_3$)((CH$_2$)$_2$CONHR$_9$), wherein $R_8$ is —C(O)H, —C(O)CH$_3$, —C(O)CH$_2$CH$_3$, —C(O)(CH$_2$)$_2$CH$_3$, —C(O)CH(CH$_3$)$_2$, —C(O)(CH$_2$)$_3$CH$_3$, —C(O)CH(CH$_3$)CH$_2$CH$_3$, —C(O)CH$_2$CH$_2$(CH$_3$)$_2$, —C(O)C(CH$_3$)$_3$, —C(O)Ph, or —C(O)CH$_2$Ph, and $R_9$ is —CH$_3$, —CH$_2$COOH, —CH$_2$CH$_3$, —CH(CH$_3$)$_2$, —(CH$_2$)$_2$CH$_3$, —(CH$_2$)$_2$SO$_3$H, C(CH$_3$)$_3$, —(CH$_2$)$_3$CH$_3$, —CH(CH$_3$)CH$_2$CH$_3$, —CH$_2$CH$_2$(CH$_3$)$_2$, an aryl group, or an alkylaryl group, $R_4$ is H, OH, or —OR$_{10}$, wherein $R_{10}$ is —C(O)H, —C(O)CH$_3$, —C(O)CH$_2$CH$_3$, —C(O)(CH$_2$)$_2$CH$_3$, —C(O)CH(CH$_3$)$_2$, —C(O)(CH$_2$)$_3$CH$_3$, —C(O)CH(CH$_3$)CH$_2$CH$_3$, —C(O)CH$_2$CH$_2$(CH$_3$)$_2$, —C(O)C(CH$_3$)$_3$, —C(O)Ph, or —C(O)CH$_2$Ph, and $R_5$ is H, CF$_3$, a $C_1$ to $C_6$ alkyl radical, a $C_1$ to $C_6$ alkenyl radical, OH, O, or a $C_1$ to $C_6$ alkoxy radical, wherein the dashed line denotes an optional double bond, with the proviso that the B ring has no double bond if the A ring has a C4-C5 double bond, and the C ring has no double bond if $X_1$ and $X_2$ form an epoxy group, or wherein the steroid having the general formula (II) is selected from the group consisting of 3α,7β,12α-trihydroxy-5β-cholane-24-acid, 3α,7β,12β-trihydroxy-5β-cholane-24-acid, 3β,7β,12α-trihydroxy-5β-cholane-24-acid, 3β,7β,12β-trihydroxy-5β-cholane-24-acid, 7β,12α-dihydroxy-3-keto-5β-cholane-24-acid, 7β,12β-dihydroxy-3-keto-5β-cholane-24-acid, 3β,7β-dihydroxy-12-keto-5β-cholane-24-acid, 3α,7β-dihydroxy-5β-cholane-24-acid, 7β-hydroxy-3-keto-5β-cholane-24-acid and 3β,7β-dihydroxy-5B-cholane-24-acid, the method comprising the step of converting a 7-deoxysteroid selected from the group consisting of 3α,12α-dihydroxy-5β-cholane-24-acid, 3α,12β-dihydroxy-5β-cholane-24-acid, 3β,12α-dihydroxy-5β-cholane-24-acid, 3β,12β-dihydroxy-5β-cholane-24-acid, 3β-hydroxy-12-keto-5β-cholane-24-acid, 3-keto,12β-hydroxy-5β-cholane-24-acid, 3-keto,12α-hydroxy-5β-cholane-24-acid, 3α-hydroxy-5β-cholane-24-acid, 3-keto-5β-cholane-24-acid and 3β-hydroxy-5β-cholane-24-acid or having the general formula (I) with cytochrome P450 enzyme:

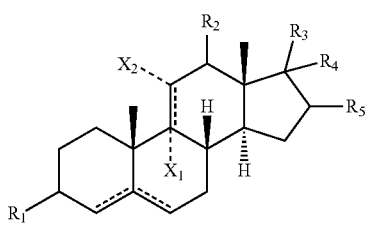

(I)

wherein $R_1$-$R_5$ and $X_1$-$X_2$ in formula (I) are as defined in formula (II), wherein the cytochrome P450 enzyme comprises an amino acid sequence which has an identity of at least 80% to the amino acid sequence of SEQ ID No. 1 or SEQ ID No. 2.

2. The method according to claim 1, wherein:

$X_1$, $X_2$, $R_4$ and $R_5$ are H, and $R_1$ und $R_2$ are independently H, OH, OR$_7$, or O, wherein $R_7$ is —C(O)H, —C(O)CH$_3$, —C(O)CH$_2$CH$_3$, —C(O)(CH$_2$)$_2$CH$_3$, —C(O)CH(CH$_3$)$_2$, —C(O)(CH$_2$)$_3$CH$_3$, —C(O)CH(CH$_3$)CH$_2$CH$_3$, —C(O)CH$_2$CH(CH$_3$)$_2$, —C(O)C(CH$_3$)$_3$, —C(O)Ph, or —C(O)CH$_2$Ph, $R_3$ is a $C_1$ to $C_{10}$ alkyl radical, a $C_1$ to $C_{10}$ alkenyl radical, —CH(CH$_3$)((CH$_2$)$_2$CO$_2$R$_9$), or —CH(CH$_3$)((CH$_2$)$_2$CONHR$_9$), wherein $R_9$ is —CH$_3$, —CH$_2$COOH, —CH$_2$CH$_3$, —CH(CH$_3$)$_2$, —(CH$_2$)$_2$CH$_3$, —(CH$_2$)$_2$SO$_3$H, C(CH$_3$)$_3$, —(CH$_2$)$_3$CH$_3$, —CH(CH$_3$)CH$_2$CH$_3$, —CH$_2$CH(CH$_3$)$_2$, an aryl group, or an alkylaryl group.

3. The method according to claim 1, wherein the aryl group is selected from the group consisting of a phenyl radical, a phenyl radical substituted with F, Cl, Br, NO$_2$ or CH$_3$, and a heteroaryl.

4. The method according to claim 1, wherein the alkylaryl group is selected from the group consisting of a benzyl group, a halogenated benzyl group in which the halogen is F, Cl or Br, and a benzyl group substituted with NO$_2$.

5. The method according to claim 1, wherein $R_1$ is OH, $R_2$ is O or OH, $R_3$ is —CH(CH$_3$)((CH$_2$)$_2$CO$_2$R$_9$), $R_4$ is H, and $R_5$ is H.

6. The method according to claim 1, wherein the enzymatic conversion takes place in the presence of at least one ferredoxin.

7. The method according to claim 1, wherein the enzymatic conversion takes place in the presence of at least one ferredoxin reductase.

8. The method according to claim 1, wherein the enzymatic conversion takes place in the presence of at least one ferredoxin and at least one ferredoxin reductase.

9. The method according to claim 1, wherein the cytochrome P450 enzyme comprises an amino acid sequence which has an identity of at least 90% to the amino acid sequence of SEQ ID No. 1 or SEQ ID No. 2.

10. The method according to claim 1, wherein the cytochrome P450 enzyme comprises an amino acid sequence which has an identity of 100% to the amino acid sequence of SEQ ID No. 1 or SEQ ID No. 2.

* * * * *

SEQUENCE LISTING

<160> NUMBER OF SEQ ID NOS: 12

<210> SEQ ID NO 1
<211> LENGTH: 397
<212> TYPE: PRT
<213> ORGANISM: Streptomyces hygroscopicus

<400> SEQUENCE: 1

Met Leu Thr Thr Ala Glu Thr Thr Ser Ile Ala Tyr Pro Phe Asn Thr
1               5                   10                  15

Ala Glu Gly Leu Ala Leu Ser Glu Arg Tyr Glu Glu Ala Arg Asn Arg
            20                  25                  30

Thr Gly Leu Leu Arg Val Arg Met Pro Tyr Gly Glu Pro Ala Trp Leu
        35                  40                  45

Val Thr Arg Tyr Ala Asp Ala Arg Leu Val Leu Gly Asp Arg Arg Phe
    50                  55                  60

Ser Arg Ala Glu Ala Leu His His Asp Glu Pro Arg Gln Ser Glu Gly
65                  70                  75                  80

Arg Arg Asp Ser Gly Ile Leu Thr Met Asp Pro Pro His Thr Arg
            85                  90                  95

Leu Arg Thr Leu Val Ala Lys Ala Phe Thr Val His Gln Val Glu Lys
            100                 105                 110

Leu Arg Pro Trp Val Arg Gln Leu Thr His Asp Leu Leu Asp Asp Leu

```
            115                 120                 125
Glu Ala Ala Gly Pro Pro Ala Asp Leu Val Asp Arg Tyr Ala Leu Pro
        130                 135                 140
Ile Pro Val Gly Val Ile Cys Ala Met Leu Gly Val Pro Gln Glu Asp
145                 150                 155                 160
Arg Pro Lys Phe Arg Val Trp Ser Asp Ala Leu Ser Thr Ser Ser
                165                 170                 175
Leu Ser Ala Glu Gln Phe Ala Arg Asn Thr Asp Glu Leu Arg Ala Tyr
            180                 185                 190
Met Ala Gly Leu Ile Glu Asp His Arg Arg Thr Pro Arg Asp Asp Ile
        195                 200                 205
Met Thr Ser Leu Ile Glu Ala Arg Asp Ala Gly Asp Arg Leu Ser Glu
    210                 215                 220
Leu Glu Leu Val Asp Leu Cys Val Gly Ile Leu Val Ala Gly His Glu
225                 230                 235                 240
Thr Thr Ala Thr Gln Ile Pro Asn Phe Val Leu Thr Leu Leu Glu His
                245                 250                 255
Pro Asp Gln Leu Arg Arg Leu Arg Glu Asp Pro Ala Leu Ile Gln Gly
            260                 265                 270
Ala Val Glu Glu Leu Leu Arg Phe Val Pro Leu Gly Val Gly Ala Ala
        275                 280                 285
Gln Ala Arg Tyr Ala Thr Glu Asp Ile Glu Val Gly Gly Thr Leu Val
    290                 295                 300
Arg Ser Gly Glu Pro Val Leu Ala Val Gly Ser Ala Asn Arg Asp
305                 310                 315                 320
Ala Leu Arg Phe Asp Glu Pro Gly Val Leu Asn Val Ala Arg Pro Thr
                325                 330                 335
Thr Gln His Leu Gly Phe Gly His Gly Val His His Cys Leu Gly Ala
            340                 345                 350
Pro Leu Ala Arg Leu Glu Leu Gln Glu Ala Leu Gly Ala Leu Ile Thr
        355                 360                 365
Arg Phe Pro Gly Leu Arg Leu Ala Gly Asp Ile Glu Trp Lys Asp Arg
    370                 375                 380
Met Leu Val Arg Gly Pro Arg Val Met Pro Ile Gly Trp
385                 390                 395

<210> SEQ ID NO 2
<211> LENGTH: 358
<212> TYPE: PRT
<213> ORGANISM: Streptomyces hygroscopicus

<400> SEQUENCE: 2

Met Pro Tyr Gly Glu Pro Ala Trp Leu Val Thr Arg Tyr Ala Asp Ala
1               5                   10                  15
Arg Leu Val Leu Gly Asp Arg Arg Phe Ser Arg Ala Glu Ala Leu His
            20                  25                  30
His Asp Glu Pro Arg Gln Ser Glu Gly Arg Arg Asp Ser Gly Ile Leu
        35                  40                  45
Thr Met Asp Pro Pro Asp His Thr Arg Leu Arg Thr Leu Val Ala Lys
    50                  55                  60
Ala Phe Thr Val His Gln Val Glu Lys Leu Arg Pro Trp Val Arg Gln
65                  70                  75                  80
Leu Thr His Asp Leu Leu Asp Asp Leu Glu Ala Gly Pro Pro Ala
                85                  90                  95
```

```
Asp Leu Val Asp Arg Tyr Ala Leu Pro Ile Pro Val Gly Val Ile Cys
                100                 105                 110

Ala Met Leu Gly Val Pro Gln Glu Asp Arg Pro Lys Phe Arg Val Trp
            115                 120                 125

Ser Asp Ala Ala Leu Ser Thr Ser Ser Leu Ser Ala Glu Gln Phe Ala
130                 135                 140

Arg Asn Thr Asp Glu Leu Arg Ala Tyr Met Ala Gly Leu Ile Glu Asp
145                 150                 155                 160

His Arg Arg Thr Pro Arg Asp Asp Ile Met Thr Ser Leu Ile Glu Ala
                165                 170                 175

Arg Asp Ala Gly Asp Arg Leu Ser Glu Leu Glu Leu Val Asp Leu Cys
            180                 185                 190

Val Gly Ile Leu Val Ala Gly His Glu Thr Thr Ala Thr Gln Ile Pro
        195                 200                 205

Asn Phe Val Leu Thr Leu Leu Glu His Pro Asp Gln Leu Arg Arg Leu
    210                 215                 220

Arg Glu Asp Pro Ala Leu Ile Gln Gly Ala Val Glu Glu Leu Leu Arg
225                 230                 235                 240

Phe Val Pro Leu Gly Val Gly Ala Ala Gln Ala Arg Tyr Ala Thr Glu
                245                 250                 255

Asp Ile Glu Val Gly Gly Thr Leu Val Arg Ser Gly Glu Pro Val Leu
            260                 265                 270

Val Ala Val Gly Ser Ala Asn Arg Asp Ala Leu Arg Phe Asp Glu Pro
        275                 280                 285

Gly Val Leu Asn Val Ala Arg Pro Thr Thr Gln His Leu Gly Phe Gly
    290                 295                 300

His Gly Val His His Cys Leu Gly Ala Pro Leu Ala Arg Leu Glu Leu
305                 310                 315                 320

Gln Glu Ala Leu Gly Ala Leu Ile Thr Arg Phe Pro Gly Leu Arg Leu
                325                 330                 335

Ala Gly Asp Ile Glu Trp Lys Asp Arg Met Leu Val Arg Gly Pro Arg
            340                 345                 350

Val Met Pro Ile Gly Trp
        355
```

<210> SEQ ID NO 3
<211> LENGTH: 1194
<212> TYPE: DNA
<213> ORGANISM: Streptomyces hygroscopicus

<400> SEQUENCE: 3

```
atgttgacca cagccgagac gacatccatc gcctatccct tcaacaccgc cgaagggctg    60
gcgctcagcg agcgttacga agaggccagg aaccgcaccg gactgctccg ggtgcggatg   120
ccctacggtg agcccgcctg gctggtcacg cggtacgccg acgcccggct ggtgctcggc   180
gaccggcgct tcagccgtgc ggaggcgctc caccacgacg agccgcggca gtccgaaggc   240
cggcgcgaca gcggcatcct gaccatggac ccgcccgacc acacccggct gcgcaccctc   300
gtcgccaagg cgttcaccgt ccaccaggtg gagaaactcc gccctgggt acgccagttg   360
acccatgacc tgctcgacga cctcgaggcc gcgggccgc cgccgatct ggtggaccgc   420
tacgccctgc ccattccggt cggcgtcatc tgcgccatgc tcggcgtccc gcaggaggac   480
cggcccaagt tcgggtctg agcgacgcc gcgctgtcca ccagtcgct gagcgccgag   540
cagttcgccc gtaacaccga cgagctgcgc gcctacatgg ccgggctgat cgaggaccac   600
```

| | |
|---|---|
| cgcaggaccc cgcgggacga catcatgacc tcgctgatcg aggcgcggga cgcgggcgac | 660 |
| cggctgtccg agctggaact cgtcgatctg tgcgtgggca tcctggtggc cgggcacgag | 720 |
| accaccgcca cccagatccc caacttcgtg ctgacgctgc tggagcaccc ggaccagctg | 780 |
| cgccggctgc gcgaggaccc cgccctgatc cagggcgccg tcgaggagct gctgcgcttc | 840 |
| gtcccgctgg gcgtgggcgc cgcccaggcc cgttacgcca ccgaggacat cgaggtgggc | 900 |
| ggcacgctgg tgcgcagcgg ggagccgtg ctggtcgccg tcggctcggc caaccgcgac | 960 |
| gcgctgcgct tcgacgaacc gggcgtgctc aacgtcgccc gccccaccac ccagcacctc | 1020 |
| ggcttcggcc acggtgtgca ccactgcctg ggcgcgcccc tggcccgtct ggagctccag | 1080 |
| gaggcgctcg gcgcgctgat cacgcgcttc ccgggcctgc ggctggccgg ggacatcgag | 1140 |
| tggaaggacc gcatgctggt ccgcgggccc cgtgtcatgc ccatcgggtg gtga | 1194 |

<210> SEQ ID NO 4
<211> LENGTH: 1077
<212> TYPE: DNA
<213> ORGANISM: Streptomyces hygroscopicus

<400> SEQUENCE: 4

| | |
|---|---|
| atgcccctacg gtgagcccgc ctggctggtc acgcggtacg ccgacgcccg gctggtgctc | 60 |
| ggcgaccggc gcttcagccg tgcggaggcg ctccaccacg acgagccgcg gcagtccgaa | 120 |
| ggccggcgcg acagcggcat cctgaccatg gacccgcccg accacaccacccg gctgcgcacc | 180 |
| ctcgtcgcca aggcgttcac cgtccaccag gtggagaaac tccgcccctg gtacgccag | 240 |
| ttgacccatg acctgctcga cgacctcgag gccgccgggc cgcccgccga tctggtggac | 300 |
| cgctacgccc tgcccattcc ggtcggcgtc atctgcgcca tgctcggcgt cccgcaggag | 360 |
| gaccggccca agttccgggt ctggagcgac gccgcgctgt ccaccagctc gctgagcgcc | 420 |
| gagcagttcg cccgtaacac cgacgagctg cgcgcctaca tggccgggct gatcgaggac | 480 |
| caccgcagga ccccgcggga cgacatcatg acctcgctga tcgaggcgcg ggacgcgggc | 540 |
| gaccggctgt ccgagctgga actcgtcgat ctgtgcgtgg gcatcctggt ggccgggcac | 600 |
| gagaccaccg ccacccagat ccccaacttc gtgctgacgc tgctggagca cccggaccag | 660 |
| ctgcgccggc tgcgcgagga ccccgccctg atccagggcg ccgtcgagga gctgctgcgc | 720 |
| ttcgtcccgc tgggcgtggg cgccgcccag gcccgttacg ccaccgagga catcgaggtg | 780 |
| ggcggcacgc tggtgcgcag cggggagccg gtgctggtcg ccgtcggctc ggccaaccgc | 840 |
| gacgcgctgc gcttcgacga accgggcgtg ctcaacgtcg cccgcccac cacccagcac | 900 |
| ctcggcttcg gccacggtgt gcaccactgc ctgggcgcgc cctggcccg tctggagctc | 960 |
| caggaggcgc tcggcgcgct gatcacgcgc ttcccggggcc tgcggctggc cggggacatc | 1020 |
| gagtggaagg accgcatgct ggtccgcggg ccccgtgtca tgcccatcgg gtggtga | 1077 |

<210> SEQ ID NO 5
<211> LENGTH: 1194
<212> TYPE: DNA
<213> ORGANISM: Artificial sequence
<220> FEATURE:
<223> OTHER INFORMATION: E.coli codon-optimized SEQ ID No. 3

<400> SEQUENCE: 5

| | |
|---|---|
| atgctgacca ccgcagaaac caccagtatt gcatatccgt ttaataccgc agaaggtctg | 60 |
| gcactgagcg aacgttatga agaagcacgt aatcgtaccg gtctgctgcg tgttcgtatg | 120 |
| ccgtatggtg aaccggcatg gctggttacc cgttatgcag atgcccgtct ggttctgggt | 180 |

```
gatcgtcgtt ttagccgtgc cgaagcactg catcacgatg aaccgcgtca gagcgaaggt      240
cgtcgtgata cggtattct gaccatggat ccgcctgatc ataccgtct gcgtaccctg        300 gttgcaaaag catttaccgt tcatcaggtt gaaaaactgc gtccgtgggt cgccagctg       360 acccatgatc tgctggatga tctggaagca gcaggtccgc ctgcagatct ggttgatcgt      420
tatgcactgc cgattccggt tggtgttatt tgtgcaatgc tgggtgttcc gcaagaagat      480
cgtcctaaat ttcgtgtttg gagtgatgca gcactgagca ccagcagcct gagcgcagaa     540
cagtttgcac gtaataccga tgaactgcgt gcatatatgg caggtctgat tgaagatcat      600
cgtcgtacac cgcgtgatga tattatgacc agcctgatcg aagcacgtga tgccggtgat      660
cgcctgagtg aactggaact ggtggatctg tgtgttggta ttctggttgc aggtcatgaa      720
accaccgcaa cccagattcc gaattttgtt ctgaccctgc tgaacatcc ggatcagctg      780 cgtcgtctgc gtgaagatcc ggcactgatt cagggtgcag ttgaagaact gctgcgtttt     840
gttccgctgg gtgtgggtgc agcacaggca cgttatgcaa ccgaagatat tgaagttggt      900
ggcaccctgg ttcgtagtgg cgaaccggtg ctggttgccg ttggtagcgc aaaccgtgat      960
gcactgcgct ttgatgaacc gggtgttctg aatgttgcac gtccgaccac acagcatctg    1020
ggttttggtc atggtgttca tcattgtctg ggtgcaccgc tggcacgtct ggaactgcaa    1080
gaagcactgg gagcactgat tacccgtttt ccgggtctgc gtctggcagg cgatattgaa    1140
tggaaagatc gtatgctggt tcgtggtccg cgtgttatgc cgattggttg gtaa           1194

<210> SEQ ID NO 6
<211> LENGTH: 1070
<212> TYPE: DNA
<213> ORGANISM: Artificial sequence
<220> FEATURE:
<223> OTHER INFORMATION: E.coli codon-optimized SEQ ID No. 4

<400> SEQUENCE: 6
atggtgaacc ggcatggctg ttacccgtt atgcagatgc ccgtctggtt ctgggtgatc       60
gtcgttttag ccgtgccgaa gcactgcatc acgatgaacc gcgtcagagc gaaggtcgtc     120
gtgatagcgg tattctgacc atggatccgc ctgatcatac ccgtctgcgt accctggttg     180
caaaagcatt taccgttcat caggttgaaa aactgcgtcc gtgggttcgc agctgacccc    240
atgatctgct ggatgatctg aagcagcag gtccgcctgc agatctggtt gatcgttatg     300
cactgccgat tccggttggt gttatttgtg caatgctggg tgttccgcaa gaagatcgtc    360
ctaaatttcg tgtttggagt gatgcagcac tgagcaccag cagcctgagc gcagaacagt    420
ttgcacgtaa taccgatgaa ctgcgtgcat atatggcagg tctgattgaa gatcatcgtc     480
gtacaccgcg tgatgatatt atgaccagcc tgatcgaagc acgtgatgcc ggtgatcgcc   540
tgagtgaact ggaactggtg gatctgtgtg ttggtattct ggttgcaggt catgaaacca   600
ccgcaaccca gattccgaat tttgttctga ccctgctgaa catccggat cagctgcgtc     660 gtctgcgtga agatccggca ctgattcagg gtgcagttga agaactgctg cgttttgttc    720
cgctgggtgt gggtgcagca caggcacgtt atgcaaccga agatattgaa gttggtggca    780
ccctggttcg tagtggcgaa ccggtgctgg ttgccgttgg tagcgcaaac cgtgatgcac    840
tgcgctttga tgaaccgggt gttctgaatg ttgcacgtcc gaccacacag catctgggtt    900
ttggtcatgg tgttcatcat tgtctgggtg caccgctggc acgtctggaa ctgcaagaag    960
cactgggagc actgattacc cgttttccgg gtctgcgtct ggcaggcgat attgaatgga   1020
```
aagatcgtat gctggttcgt ggtccgcgtg ttatgccgat tggttggtaa        1070

<210> SEQ ID NO 7
<211> LENGTH: 107
<212> TYPE: PRT
<213> ORGANISM: Pseudomonas putida
<220> FEATURE:
<221> NAME/KEY: MISC_FEATURE
<222> LOCATION: (1)..(1)
<223> OTHER INFORMATION: Xaa is methionine or no amino acid residue

<400> SEQUENCE: 7

```
Xaa Ser Lys Val Val Tyr Val Ser His Asp Gly Thr Arg Arg Glu Leu
1               5                   10                  15

Asp Val Ala Asp Gly Val Ser Leu Met Gln Ala Ala Val Ser Asn Gly
            20                  25                  30

Ile Tyr Asp Ile Val Gly Asp Cys Gly Gly Ser Ala Ser Cys Ala Thr
        35                  40                  45

Cys His Val Tyr Val Asn Glu Ala Phe Thr Asp Lys Val Pro Ala Ala
50                  55                  60

Asn Glu Arg Glu Ile Gly Met Leu Glu Cys Val Thr Ala Glu Leu Lys
65                  70                  75                  80

Pro Asn Ser Arg Leu Cys Cys Gln Ile Ile Met Thr Pro Glu Leu Asp
                85                  90                  95

Gly Ile Val Val Asp Val Pro Asp Arg Gln Trp
            100                 105
```

<210> SEQ ID NO 8
<211> LENGTH: 422
<212> TYPE: PRT
<213> ORGANISM: Pseudomonas putida

<400> SEQUENCE: 8

```
Met Asn Ala Asn Asp Asn Val Val Ile Val Gly Thr Gly Leu Ala Gly
1               5                   10                  15

Val Glu Val Ala Phe Gly Leu Arg Ala Ser Gly Trp Glu Gly Asn Ile
            20                  25                  30

Arg Leu Val Gly Asp Ala Thr Val Ile Pro His His Leu Pro Pro Leu
        35                  40                  45

Ser Lys Ala Tyr Leu Ala Gly Lys Ala Thr Ala Glu Ser Leu Tyr Leu
    50                  55                  60

Arg Thr Pro Asp Ala Tyr Ala Ala Gln Asn Ile Gln Leu Leu Gly Gly
65                  70                  75                  80

Thr Gln Val Thr Ala Ile Asn Arg Asp Arg Gln Val Ile Leu Ser
                85                  90                  95

Asp Gly Arg Ala Leu Asp Tyr Asp Arg Leu Val Leu Ala Thr Gly Gly
            100                 105                 110

Arg Pro Arg Pro Leu Pro Val Ala Ser Gly Ala Val Gly Lys Ala Asn
        115                 120                 125

Asn Phe Arg Tyr Leu Arg Thr Leu Glu Asp Ala Glu Cys Ile Arg Arg
    130                 135                 140

Gln Leu Ile Ala Asp Asn Arg Leu Val Val Ile Gly Gly Gly Tyr Ile
145                 150                 155                 160

Gly Leu Glu Val Ala Ala Thr Ala Ile Lys Ala Asn Met His Val Thr
                165                 170                 175

Leu Leu Asp Thr Ala Ala Arg Val Leu Glu Arg Val Thr Ala Pro Pro
            180                 185                 190
```

Val Ser Ala Phe Tyr Glu His Leu His Arg Glu Ala Gly Val Asp Ile
            195                 200                 205

Arg Thr Gly Thr Gln Val Cys Gly Phe Glu Met Ser Thr Asp Gln Gln
        210                 215                 220

Lys Val Thr Ala Val Leu Cys Glu Asp Gly Thr Arg Leu Pro Ala Asp
225                 230                 235                 240

Leu Val Ile Ala Gly Ile Gly Leu Ile Pro Asn Cys Glu Leu Ala Ser
                245                 250                 255

Ala Ala Gly Leu Gln Val Asp Asn Gly Ile Val Ile Asn Glu His Met
            260                 265                 270

Gln Thr Ser Asp Pro Leu Ile Met Ala Val Gly Asp Cys Ala Arg Phe
        275                 280                 285

His Ser Gln Leu Tyr Asp Arg Trp Val Arg Ile Glu Ser Val Pro Asn
    290                 295                 300

Ala Leu Glu Gln Ala Arg Lys Ile Ala Ala Ile Leu Cys Gly Lys Val
305                 310                 315                 320

Pro Arg Asp Glu Ala Ala Pro Trp Phe Trp Ser Asp Gln Tyr Glu Ile
                325                 330                 335

Gly Leu Lys Met Val Gly Leu Ser Glu Gly Tyr Asp Arg Ile Ile Val
            340                 345                 350

Arg Gly Ser Leu Ala Gln Pro Asp Phe Ser Val Phe Tyr Leu Gln Gly
        355                 360                 365

Asp Arg Val Leu Ala Val Asp Thr Val Asn Arg Pro Val Glu Phe Asn
    370                 375                 380

Gln Ser Lys Gln Ile Ile Thr Asp Arg Leu Pro Val Glu Pro Asn Leu
385                 390                 395                 400

Leu Gly Asp Glu Ser Val Pro Leu Lys Glu Ile Ile Ala Ala Ala Lys
                405                 410                 415

Ala Glu Leu Ser Ser Ala
            420

<210> SEQ ID NO 9
<211> LENGTH: 324
<212> TYPE: DNA
<213> ORGANISM: Pseudomonas putida
<220> FEATURE:
<221> NAME/KEY: misc_feature
<222> LOCATION: (1)..(1)
<223> OTHER INFORMATION: n is A or no nucleotide
<220> FEATURE:
<221> NAME/KEY: misc_feature
<222> LOCATION: (2)..(2)
<223> OTHER INFORMATION: n is T or no nucleotide
<220> FEATURE:
<221> NAME/KEY: misc_feature
<222> LOCATION: (3)..(3)
<223> OTHER INFORMATION: n is G or no nucleotide

<400> SEQUENCE: 9
nnntctaaag tagtgtatgt gtcacatgat ggaacgcgtc gcgaactgga tgtggcggat      60
ggcgtcagcc tgatgcaggc tgcagtctcc aatggtatct acgatattgt cggtgattgt     120
ggcggcagcg ccagctgtgc cacctgccat gtctatgtga acgaagcgtt cacggacaag     180
gtgcccgccg ccaacgagcg ggaaatcggc atgctggagt cgtcacggc cgaactgaag      240 ccgaacagca ggctctgctg ccagatcatc atgacgcccg agctggatgg catcgtggtc     300
gatgttcccg ataggcaatg gtaa                                             324

<210> SEQ ID NO 10

```
<211> LENGTH: 1269
<212> TYPE: DNA
<213> ORGANISM: Pseudomonas putida

<400> SEQUENCE: 10
atgaacgcaa acgacaacgt ggtcatcgtc ggtaccggac tggctggcgt tgaggtcgcc      60
ttcggcctgc gcgccagcgg ctgggaaggc aatatccggt tggtggggga tgcgacggta     120
attccccatc acctaccacc gctatccaaa gcttacttgg ccggcaaagc cacagcggaa     180
agcctgtacc tgagaacccc agatgcctat gcagcgcaga acatccaact actcggaggc     240
acacaggtaa cggctatcaa ccgcgaccga cagcaagtaa tcctatcgga tggccgggca     300
ctggattacg accggctggt attggctacc ggagggcgtc aagacccct accggtggcc      360
agtggcgcag ttggaaaggc gaacaacttt cgatacctgc gcacactcga ggacgccgag     420
tgcattcgcc ggcagctgat tgcggataac cgtctggtgg tgattggtgg cggctacatt     480
ggccttgaag tggctgccac cgccatcaag gcgaacatgc acgtcaccct gcttgatacg     540
gcagcccggg ttctggagcg ggttaccgcc ccgccggtat cggccttta cgagcaccta      600
caccgcgaag ccggcgttga catacgaacc ggcacgcagg tgtgcgggtt cgagatgtcg     660
accgaccaac agaaggttac tgccgtcctc tgcgaggacg gcacaaggct gccagcggat     720
ctggtaatcg ccgggattgg cctgatacca aactgcgagt tggccagtgc ggccggcctg     780
caggttgata acgcatcgt gatcaacgaa cacatgcaga cctctgatcc cttgatcatg      840
gccgtcggcg actgtgcccg atttcacagt cagctctatg accgctgggt cgtatcgaa      900
tcggtgccca atgccttgga gcaggcacga agatcgccg ccatcctctg tggcaaggtg      960
ccacgcgatg aggcggcgcc ctggttctgg tccgatcagt atgagatcgg attgaagatg    1020
gtcggactgt ccgaagggta cgaccggatc attgtccgcg gctctttggc gcaacccgac    1080
ttcagcgttt tctacctgca gggagaccgg gtattggcgg tcgatacagt gaaccgtcca    1140
gtggagttca accagtcaaa acaaataatc acggatcgtt tgccggttga accaaaccta    1200
ctcggtgacg aaagcgtgcc gttaaaggaa atcatcgccg ccgccaaagc tgaactgagt    1260
agtgcctga                                                             1269

<210> SEQ ID NO 11
<211> LENGTH: 327
<212> TYPE: DNA
<213> ORGANISM: Artificial sequence
<220> FEATURE:
<223> OTHER INFORMATION: E.coli codon-optimized SEQ ID No. 9
<220> FEATURE:
<221> NAME/KEY: misc_feature
<222> LOCATION: (1)..(1)
<223> OTHER INFORMATION: n is A or no nucleotide
<220> FEATURE:
<221> NAME/KEY: misc_feature
<222> LOCATION: (2)..(2)
<223> OTHER INFORMATION: n is T or no nucleotide
<220> FEATURE:
<221> NAME/KEY: misc_feature
<222> LOCATION: (3)..(3)
<223> OTHER INFORMATION: n is G or no nucleotide

<400> SEQUENCE: 11
nnnatgagca aagtggtcta tgtgtcgcat gatggaacac gccgtgagtt agacgtcgct      60
gatggtgtat ccctgatgca agcagcggtt agcaatggca tttacgacat cgttggcgat     120
tgtggtggta gtgcgtcatg tgcaacgtgt cacgtgtatg ttaacgaagc gtttaccgat     180
aaggtgcctg ctgccaatga acgcgagatt ggcatgctgg aatgcgtaac tgccgaactc     240
```

-continued

```
aaaccgaact ctcgcctgtg ctgccagatc atcatgaccc cggaattgga cgggattgtc     300
gttgatgtgc cagatcgtca gtggtaa                                         327

<210> SEQ ID NO 12
<211> LENGTH: 1269
<212> TYPE: DNA
<213> ORGANISM: Artificial sequence
<220> FEATURE:
<223> OTHER INFORMATION: E.coli codon-optimized SEQ ID No. 10

<400> SEQUENCE: 12
atgaacgcca atgataatgt tgttattgtt ggcaccggtc tggcaggcgt tgaagttgca      60
tttggtctgc gtgcaagcgg ttgggaaggt aatattcgtc tggttggtga tgcaaccgtt     120
attccgcatc atctgcctcc gctgagcaaa gcatatctgg caggtaaagc aaccgcagaa     180
agcctgtatc tgcgtacacc ggatgcctat gcagcacaga atattcagct gctgggtggt     240
acacaggtta ccgcaattaa tcgtgatcgt cagcaggtta ttctgagtga tggtcgtgca     300
ctggattatg atcgtctggt gctggcaacc ggtggtcgtc cgcgtccgct gccggttgca     360
agtggtgcag ttggtaaagc caataacttt cgttatctgc gcaccctgga agatgcagaa     420
tgtattcgtc gtcagctgat tgcagataat cgcctggttg tgattggtgg tggttatatt     480
ggtctggaag ttgcagcaac cgccattaaa gcaaatatgc atgttaccct gctggatacc     540
gcagcacgtg ttctggaacg tgttaccgca ccgcctgtta gcgccttta tgaacatctg     600 catcgtgaag ccggtgttga tattcgtacc ggcacccagg tttgtggttt tgaaatgagc     660
accgatcagc agaaagttac cgcagttctg tgtgaagatg gcacccgtct gcctgcagat     720
ctggttattg caggtattgg cctgattccg aattgtgaac tggcaagcgc agcaggtctg     780
caggttgata tggtattgt tattaacgaa cacatgcaga ccagcgatcc gctgattatg     840
gcagttggtg attgtgcacg tttttcatagc cagctgtatg atcgttgggt tcgtattgaa     900
agcgttccga atgcactgga acaggcacgt aaaattgcag caattctgtg tggtaaagtt     960
ccgcgtgatg aagcagcacc gtggttttgg agcgatcagt atgaaattgg tctgaaaatg    1020
gttggtctga gcgaaggtta tgatcgcatt attgttcgtg gtagcctggc acagccggat    1080
ttttcagttt tttatctgca gggtgatcgt gtgctggcag ttgataccgt taatcgtccg    1140
gttgaattta ccagagcaa acaaattatc accgatcgtc tgccggtgga accgaatctg    1200
ctgggagatg aaagcgtgcc gctgaaagaa attattgcag cagcaaaagc agaactgagc    1260
agcgcataa                                                            1269
```